United States Patent
Muntermann

(10) Patent No.: US 6,304,776 B1
(45) Date of Patent: Oct. 16, 2001

(54) PROCESS AND APPARATUS FOR THE DETECTION OF CATHETER-TISSUE CONTACT, AND ALSO OF INTERACTIONS WITH THE TISSUE CATHETER ABLATION

(76) Inventor: Axel Muntermann, Sudetenstrasse 7-9, D-35583 Wetzlar (DE)

( * ) Notice: Subject to any disclaimer, the term of this patent is extended or adjusted under 35 U.S.C. 154(b) by 0 days.

(21) Appl. No.: 09/402,222
(22) PCT Filed: Apr. 1, 1998
(86) PCT No.: PCT/DE98/00932
§ 371 Date: Dec. 23, 1999
§ 102(e) Date: Dec. 23, 1999
(87) PCT Pub. No.: WO98/43547
PCT Pub. Date: Oct. 8, 1998

(30) Foreign Application Priority Data

Apr. 1, 1997 (DE) ............................................. 197 13 234
Sep. 17, 1997 (DE) ............................................. 197 40 976

(51) Int. Cl.[7] ..................................................... A61B 5/05
(52) U.S. Cl. ........................... 600/547; 600/443; 600/523
(58) Field of Search ................................... 600/547, 443, 600/523

(56) References Cited

U.S. PATENT DOCUMENTS 5,419,767 * 5/1995 Eggers et al. ......................... 604/114
5,462,545 * 10/1995 Wang et al. ........................... 606/41
5,562,722 * 10/1996 Racz et al. ........................... 607/117
5,704,908 * 1/1998 Hofmann et al. ....................... 604/21
6,066,139 * 5/2000 Ryan et al. ........................... 606/50

FOREIGN PATENT DOCUMENTS 0 391 233 A2   3/1990 (EP) ............................. A61B/17/39
WO 96/41569  12/1996 (WO) ........................... A61B/5/0402

* cited by examiner

*Primary Examiner*—John P. Lacyk
*Assistant Examiner*—Pamela L Wingood

(57) ABSTRACT

In a process and an apparatus for the detection of the contact and/or the interaction of a catheter arranged in a patient's vessel, in particular in a patient's blood stream, with the patient's tissue, in order to contribute to an improved detection of this contact or to make it possible for the first time to permit statements during an ablation process regarding the ablation depth or regarding the interaction with the tissue, a device is provided for the detection of a voltage at at least one catheter electrode, wherein the voltage between the catheter electrode and a further electrode is measured, and wherein the further electrode is a neutral electrode in contact with the patient's body or a further electrode installed on the catheter.

24 Claims, 4 Drawing Sheets

PROCESS AND APPARATUS FOR THE DETECTION OF CATHETER-TISSUE CONTACT, AND ALSO OF INTERACTIONS WITH THE TISSUE CATHETER ABLATION

The invention relates to a process and an apparatus for the detection of contact with tissue by a catheter which is arranged in a patient's vessel, particularly in a patient's blood stream, and furthermore to a process and an apparatus for the detection of the interaction of high frequency energy with the patient's tissue.

In many medical applications or treatments it is of the greatest importance for the doctor to detect, to follow, and in many cases also to record, the contact of an instrument with the patient's body, with high precision, since the result of the treatment frequently depends on this to a considerable degree.

In particular, in catheter ablation, the desired treatment effect is as a rule only obtained when a contact between the ablation catheter and the patient's tissue to be treated can be insured during the whole period during which ablation power is delivered.

Resistance measurements between at least two catheter electrodes, or the cathode electrodes and a neutral electrode arranged on the patient's body, were heretofore carried out for the detection of catheter-tissue contact. However, this manner of proceeding is disadvantageous, particularly in high frequency catheter ablation, since the resistance measurement is connected in principle with a flow or current through the region to be measured. However, additional currents are thereby introduced during the ablation, and can cause severe disturbances, for example in the detection of EKG signals. If direct current resistance measurement methods are used, in order to avoid high frequency signals which affect the detection of EKG signals, undesired electrolytic effects are produced, and lead to a further chemical stress for the patient. Furthermore, resistance measurements are difficult to carry out and subject to disturbance, where corrosive effects and surface contamination hinder the flow of current or falsify the measurement result. Such a situation is however already present in the field of medical applications, since here the blood or body fluids of the patient have salts or coagulating substances which can undesirably interact with the surface of electrodes or contacts. Furthermore, the tissue contact during the ablation can be judged by means of impedance measurements, only with difficulty, since many factors can affect the impedance value.

Consequently, the invention has as its object to avoid the abovementioned disadvantage and to contribute to an improved detection of contact between the catheter and the patient's tissue. This object is attained in a most surprising manner by a process according to claim 1 and an apparatus according to claim 11.

The inventor has found in a surprising manner that in many cases, when electrodes are placed on a patient's tissue, in particular in the case of tissues bathed in blood, voltages arise between the electrodes and in particular during HF ablation. The preferably metallic electrode of an ablation catheter for example produces the voltage signal shown in FIG. 1 and obtained according to the invention in the measuring arrangement shown in FIG. 2.

The inventor has found in a most surprising manner that a catheter arranged in the blood stream produces at first only a very weak voltage signal, denoted here by $U_0$, in contrast to which there then follows an abrupt rise in voltage when the catheter electrode comes into contact with the tissue. The instantaneous value or amplitude of the voltage signal derived in this manner represents a measure of the quality of the cathetertissue contact and can be detected without the use of additional external currents. Consequently in the manner according to the invention no electrolytic processes arise, and as a result of this, further measurements such as the recording of EKG signals, for example, are not adversely affected.

It has furthermore been found that the voltage measurement according to the invention is clearly superior to the conventional resistance measurement in regard to the measurement data obtained. Firstly, the voltage is an extremely accurate measure for the contact of the catheter electrode with the tissue, while an impedance measurement during the ablation permits only conditional conclusions about the tissue contact of the catheter, and secondly this signal appears nearly without any time delay, which makes this suitable for real time measurements.

It has further been found in a particularly surprising manner that the height of the measured signal is very precisely correlated with the temperature of the tissue, particularly that of a tissue which is heated during ablation. It could be shown by parallel measurement processes that with the invention, temperature values of the tissue in contact with the catheter could already be measured with an accuracy of $\pm 1°$ C. Furthermore, accuracies of $\pm 2°$ C. could be measured with simple means, i.e., simple, high ohmic voltage measurement devices. Here the temperature is in regular, linear proportion to the measured voltage, which made it possible to allocate standardized voltage measurement values to the same ablation catheter or to a group of catheters of like construction.

Since voltages can in principle also be measured without current, for example by impressing a counter-voltage of equal height, or by measuring with very high-ohmic instrumentation amplifiers, transition resistances of contacts within the measurement region play a far smaller part than in all the conventional measurement processes. Consequently, the apparatus according to the invention or the process according to the invention is exposed to fewer disturbances and can be used more conveniently and reliably. Furthermore, thermal (transit) resistances, and also thermal capacitances, of the catheter have far smaller effects on the accuracy and also speed of the measurement of the temperature.

It has been found in a further most surprising manner that in catheter ablation itself, its results can be considerably improved. If, for example, the catheter temperature is taken as the control value, as in the conventional catheter temperature control, and thus as a measure of the energy delivery, it can happen that with a relatively cold catheter, for example, at a temperature of only about 40° C., a marked lesion in the tissue is already produced, when the catheter is located in very close contact with the tissue and hence a large portion of the ablation energy could be delivered into it.

The conventional, pure temperature control with thermal sensors would not have detected the lesion in this case. Furthermore, only small lesion effect or ablation effect take place even at a higher catheter temperature when the catheter-tissue contact is very poor. In both cases, an inexact or false opinion of the result of the treatment could be derived from the conventional processes and apparatuses.

The starting point according to the invention, however, is that it is always insured by the voltage signals which arise and are detected that the energy delivery takes place substantially into the tissue, and consequently in the invention the power delivered by the catheter is allocated more directly and exactly to a treatment effect. Furthermore, after the abrupt voltage rise has detected the catheter/tissue contact, the absolute height of the voltage signal can be used for very accurate temperature measurement.

Furthermore, it is possible to use the arising voltage signal for the control or monitoring of the ablation process itself. If, for example, during high frequency ablation, the voltage signals are determined during the delivery of high frequency power, and if switching off or at least a reduction of the delivery of high frequency power is effected on exceeding or falling below the value, it is always insured that the high frequency power was substantially delivered into the patient's tissue, and this leads to a treatment with overall cooler catheter electrodes and higher action.

It is furthermore advantageous to integrate the voltage signal and thus to attain a statement concerning the interaction, i.e., concerning the temperature acting and the treatment time.

Furthermore, contaminations of the catheter due to coagulation occur in only a very small amount because of the lower catheter temperatures which have been made possible based on the precise measurement, and a discontinuance of treatment caused by such contaminations, and the resulting increased stress for the patient, are avoided.

If the switching off, or at least the reduction, of the delivery of the high frequency power is effected when there is a rapid rise or fall of the potential values, the vaporization of the treated tissues can hereby also be prevented or at least greatly limited, since now a very rapid regulation is possible, and undesired overheating of the tissues no longer occurs.

In a most surprising manner, it has furthermore been found that the potentials or voltage signals according to the invention can always be very reliably detected while the high frequency ablation is being carried out, independently of whether the high frequency signals for the ablation are applied continuously or as pulses. If the high frequency power delivered by the catheter is integrated over time, as long as the voltage signals are situated above a predeterminable boundary value which insures that a catheter/tissue contact is present, and if the integrated power is calculated as the ablation energy delivered into the tissue up to this point in time, not only can the progress of the treatment result be displayed to the doctor who is performing the treatment, but also, with a correspondingly programmed control device, the treatment can be ended by an automated switching off or reduction of the high frequency power when a predetermined energy value is reached. A far higher degree of treatment safety can hereby be provided, than was possible with the processes heretofore. It is hereby possible for the first time to already determine the ablation action in the course of the treatment, by the integration of the delivered power, and to display it in real time to the doctor performing the treatment.

Furthermore, in a further development according to the invention, the doctor performing the treatment can predetermine tissue depths which are allocated to the time integral of the measured potential. The apparatus according to the invention can then either end the whole ablation process after the predetermined value is reached, or in the case of catheters having several electrodes, local associated sections of the catheter within which the predetermined values were reached can be switched off, or a low power can be supplied to these.

If catheters with several ablation electrodes are used for this purpose in a preferred manner according to the invention, the signal data of the respective special electrode can be determined, calculated and displayed, and the course of the treatment can be programmably ended, allocated to the treatment site. Hereby optimized data for the treatment can also be already predetermined, locally allocated, before the beginning of the treatment, and a treatment which is optimized for the respective patient can be carried out.

The invention is described in detail hereinbelow by means of preferred embodiments and with reference to the accompanying drawings.

The invention is described hereinbelow with reference to preferred embodiments and first with reference to FIGS. 1 and 4.

Figure 1:
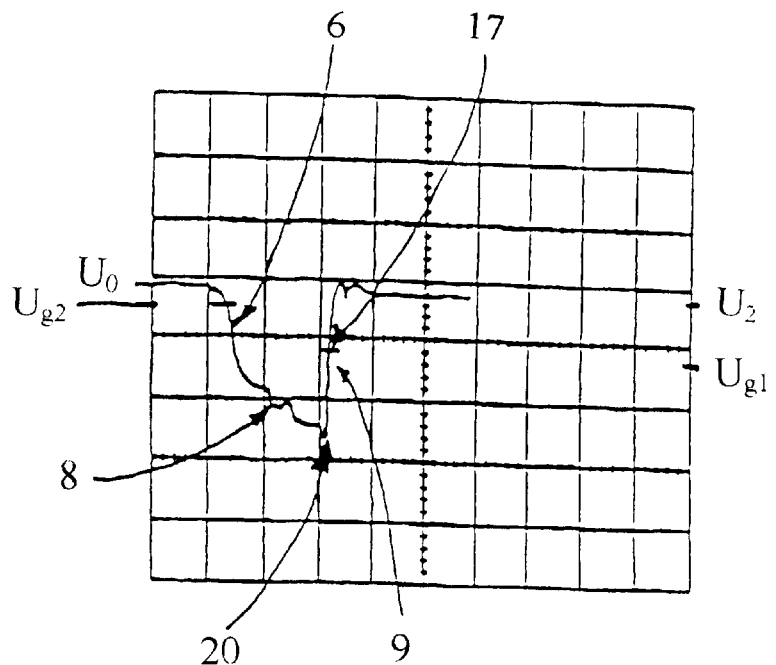
FIG. 1 shows the signal form of the voltage according to the invention, as it appears in a system with a neutral platinum electrode and also a platinum catheter electrode, when there is a catheter electrode—tissue contact which is limited in time.

In a first embodiment, which is kept as simple as possible for illustration, the voltage signal shown in FIG. 1 is recovered with the voltage measurement apparatus 1, which is preceded by a low pass filter 2.

The voltage tappings a and b of the low pass filter are connected to platinum electrodes of a bipolar catheter, as was described, for example, in PCT/DE96/00638.

However, the catheter 3, for carrying out the present invention, generally does not need any additional means for determination of the catheter temperature, such as thermal sensors for example, although this is not excluded by the invention.

As an alternative to the tapping of the voltage at the catheter electrodes a and b, the voltage can also be determined between the neutral electrode(s) 4 and one of the electrodes a, b of the catheter 3, or determined in relation to the place of the respective catheter electrode a, b.

The low pass filter 2 of the first embodiment according to the invention is connected to a storage oscilloscope of type Hameg HM 1007, which in the usual manner represents a two-dimensional display apparatus for display of the time course of the voltage.

Figure 3:
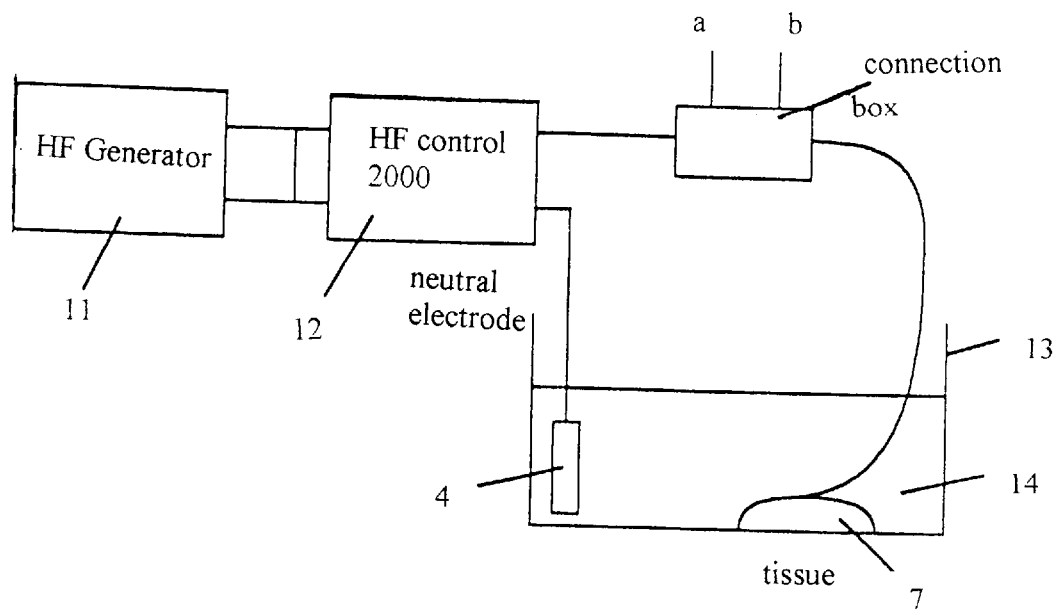
FIG. 3 shows a laboratory setup for the standardization or calibration and also acquiring measurement data by means of a pig heart.

The signal form of the time course of voltage was first obtained with the measurement setup shown in FIG. 3; the timebase was 20 sec TIME/DIV and the displayed voltage corresponded to 10 mV VOLTS/DIV. The at first low flat section 5 of the base signal $U_0$ represents the voltage when the catheter 3 is in the blood stream, and shows a clearly marked signal flank 6 as soon as the catheter 3 comes into contact with the tissue 7.

The signal shoulder 8 which extends substantially flat after the abrupt rise of the signal flank 6 shows a time modulation which can be attributed to the mechanical catheter-tissue contact between the catheter electrode b and the tissue 7 in relation to the neutral electrode 4 or the electrode a, or can be connected to the production and transport of chemical substances which arise due to electrical potentials at the location of the catheter.

If the catheter is removed from the tissue, a falling signal flank 9 occurs, which dies away into a base signal $U_2$ which is slightly increased relative to the base signal 0.

The abrupt rise 6 and fall 9 of the signal flank indicates with high certainty the generation and also ending of a catheter/tissue contact.

The construction used for the recovery of the signal form shown in FIG. 1 is schematically shown in FIG. 3 in the form of a stationary measuring construction, which is used for standardization and calibration. A HF generator 11 is connected to the appliance described in the abovecited PCT Application for the controlled delivery of HF power to the catheter 3, which has several ablation electrodes, and supplies pulsed high frequency power to the electrodes of the catheter 3.

However, in an alternative development according to the invention, the high frequency power can also be supplied continuously in time to the catheter 3.

Arranged within a trough 13 are the neutral electrode 4 and also the tissue 7, on which ablation processes are effected by means of the catheter 3. The trough 11 can be filled either with blood or with another liquid, in order to simulate the conditions present in the patient's body.

The neutral electrode 4 and also the electrodes a and b of the catheter are platinum coated or consist of platinum, and are cleaned with formalin or formaldehyde gas immediately before use, so that substantially no surface residues remain on the catheter or on the neutral electrode 4.

It has been found that the cleaning with formalin or formaldehyde gas led to very good and sufficiently reproducible measurement results, which were very exactly traceable over a time span of several days. However, it is also within the scope of the invention to use other cleaning processes in order to obtain an electrode surface which is substantially free from residues.

Furthermore the use is not excluded of other metals or chemical substances which are capable of producing the voltage according to the invention or similar voltages which arise on contact of the cathode electrodes with the tissue. For this purpose, in the sense according to the invention, but however without limitation of its generality, the starting point was that free radicals or at least chemical substances are produced during the catheter ablation and give rise to the potentials according to the invention. A further starting point was that in the case of a strong interaction of the high frequency power with the tissue an increased emergence of the abovementioned substances from the tissue takes place, and the apparatus according to the invention can provide direct evidence regarding the damage or lesion action produced in the tissue.

Figure 5:
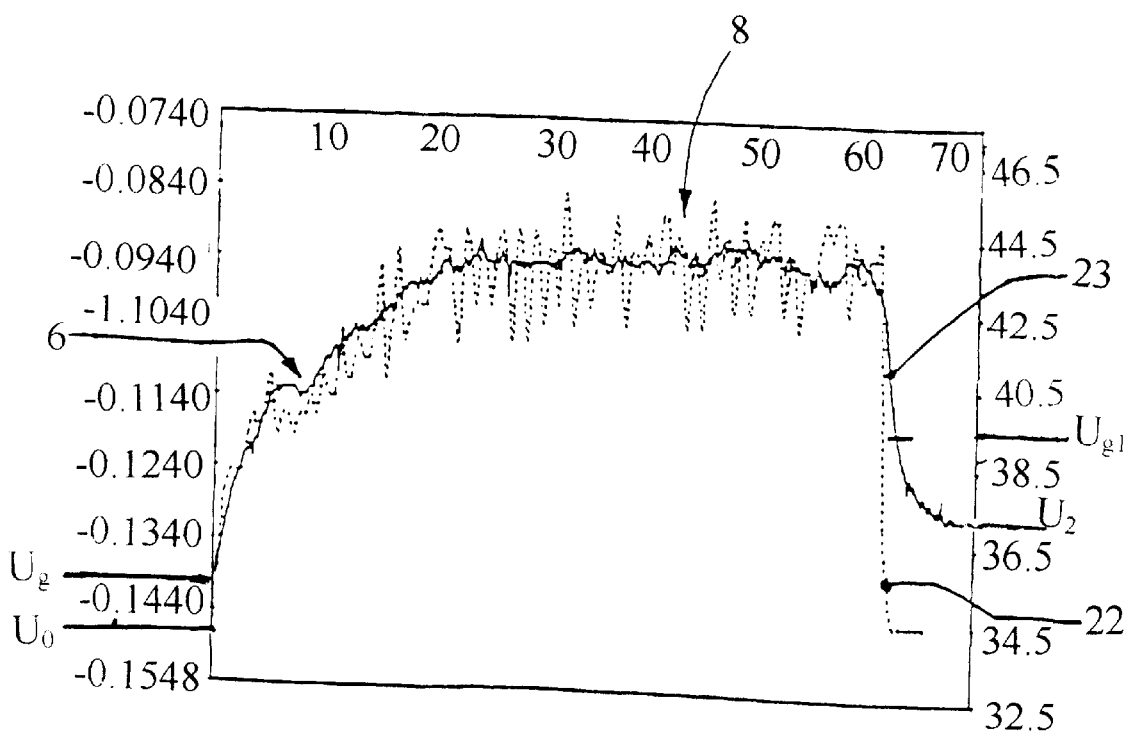
FIG. 5 shows a comparison of the potential values recovered according to the invention with locally allocated temperature values recovered at an ablation catheter during catheter ablation in a living heart.

Reference is next made to FIG. 5, which represents the comparison of the potential values according to the invention with temperatures which were determined at the same time at the place of the potential measurement. The correspondence of the temperature values, shown dashed, with the potential value 23, shown by a full line, agrees well with the previously stated model, as expected, since also chemical potentials are substantially temperature-independent. However, if the temperature after the treatment falls further, as shown on the right-hand side of FIG. 5, the potential only falls to the increased value $U_2$, which can be well explained by the presence of the chemical substances discussed hereinabove.

A distinction between a loss of mechanical contact and a fall of temperature is easily possible in that the delivered power is determined and from it a threshold value is formed. This threshold value gives the minimum expected voltage value, and can effect the shutting off of the delivery of ablation energy when the actual value falls below the threshold.

Figure 6:
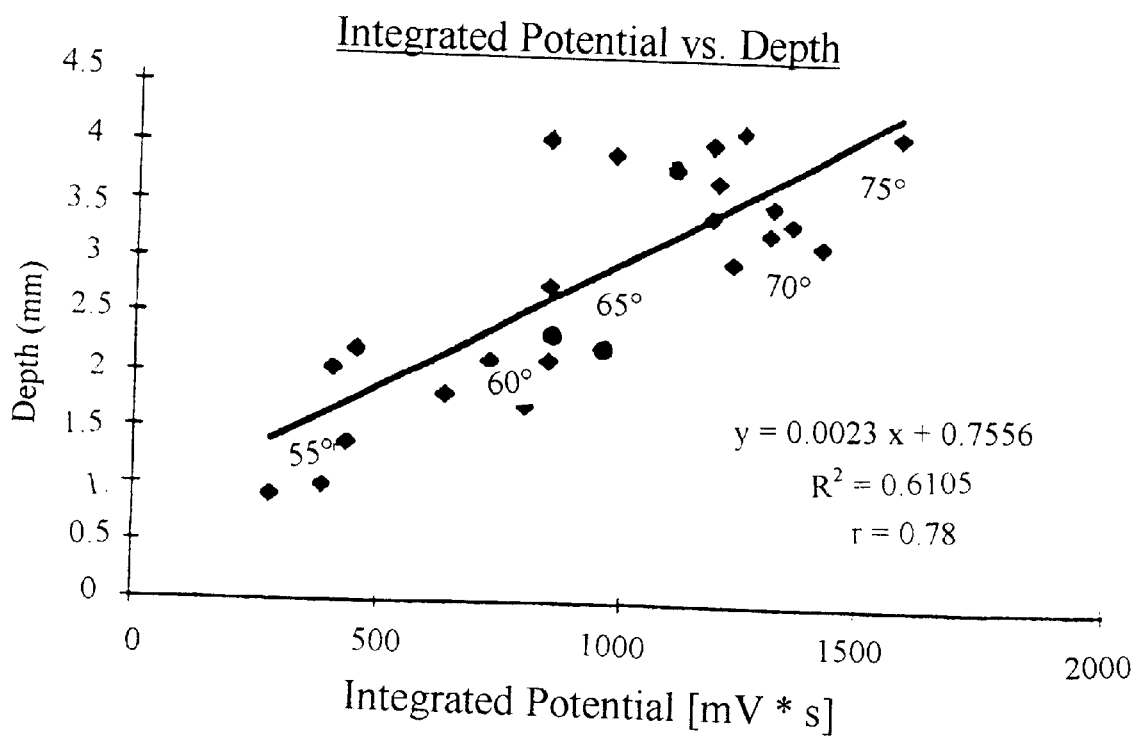
FIG. 6 shows a comparison of the values of the time integral of the potential values recovered according to the invention with various temperatures of the ablation catheter reached during catheter ablation.

Further clear support of the explanatory model of the arising potential is given in FIG. 6, which shows the dependence of the depth of the lesions produced in the tissue of a patient in HF ablation on the time integral of the potentials which arise. Over a temperature range of the ablation catheter of more than 20° C., namely from less than 55° C. up to more than 75° C. as the ablation temperature, these values are well correlated with each other. Consequently, with known catheter properties, the time integral of the potential can be sufficient to obtain suitable evidence on the course of the treatment, without having additionally to determine temperature values.

Such catheters could dispense with thermal sensors and consequently be produced more simply, at more favorable cost, and with a smaller diameter.

It is furthermore within the scope of the invention, for simpler embodiments, to limit the delivered power of the HF ablation generator, without temperature measurement, so that predetermined maximum temperatures are never exceeded, so that in this case also a suppression of undesired coagulation processes and a vaporization of the tissue are stopped.

In order to improve the accuracy of the measurement, or the correlation between the magnitudes shown in FIG. 6, a measurement of the potential values, preferably in real time, and weighted by or functionally connected to the delivered power, can be undertaken by the evaluation unit 18.

Figure 2:
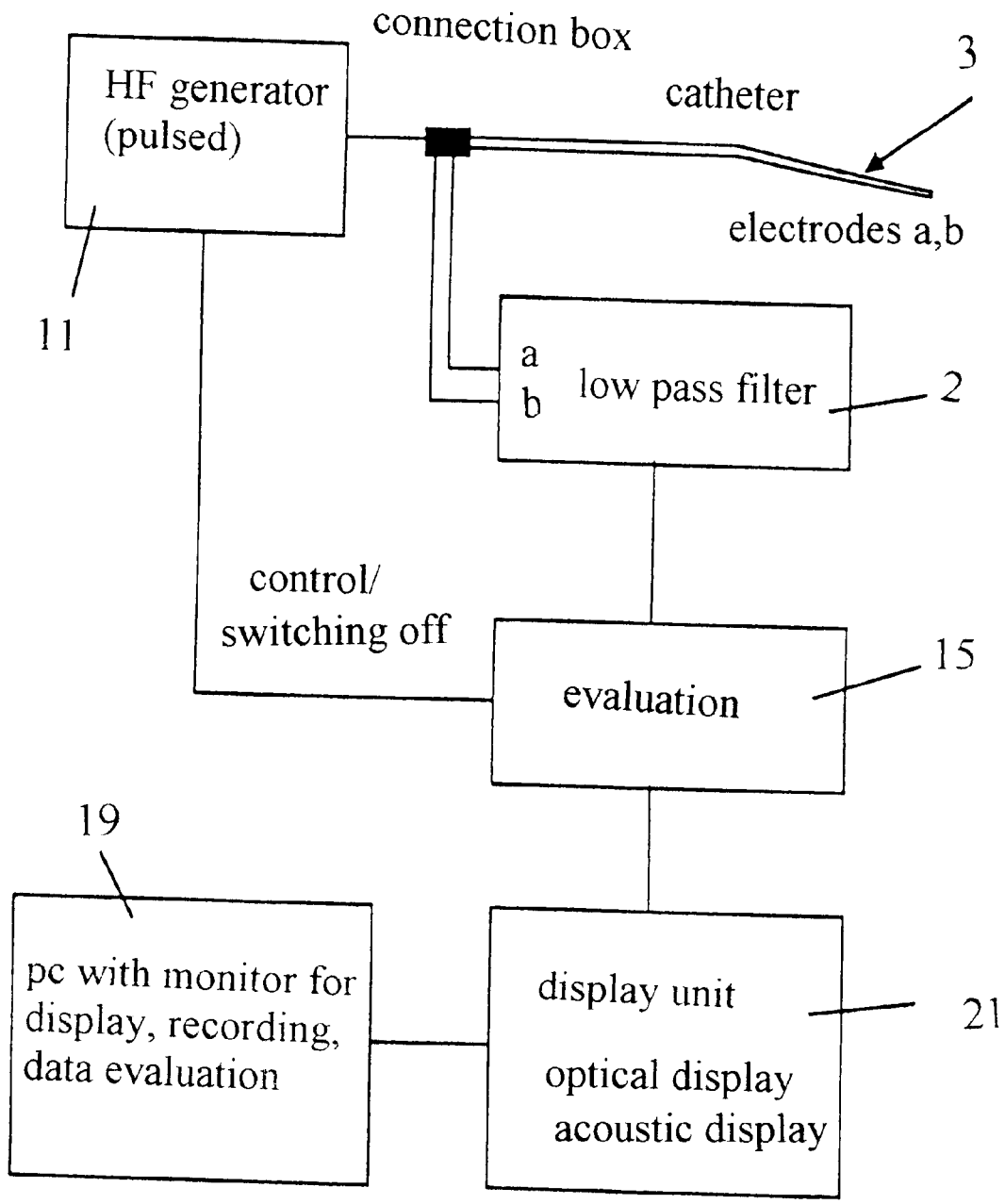
FIG. 2 is a schematic representation for carrying out the invention, with a catheter and also an apparatus, which for example corresponds to that described in PCT/DE96/00638, but however further developed according to the invention.

A further embodiment according to the invention is shown in FIG. 2, in which the generator 11, operated in pulsed mode and described in the abovementioned PCT Application, is connected to the catheter 3 and also its catheter electrodes a and b. The catheter electrodes a and b are either the ablation electrodes themselves or associated measurement electrodes which are arranged in their neighborhood and connected to the low pass filter 2 that filters out both the high frequency signal and also ripple signal interference.

The evaluation unit 15 which follows includes the voltage measuring device 1, which has a high-ohmic input resistance of at least more than 100 k$\Omega$ and preferably several M$\Omega$, in order to suppress any additional current flow to the ablation process and also of further measurement processes to a no longer measurable value. In the sense according to the invention, a high-ohmic voltage measurement is a voltage measurement which, during the performance of the ablation or of the measurement of EKG signals, for example, is no longer noticeable or is no longer detectable.

In a particularly preferred embodiment, for example a storage oscilloscope which can be connected to a personal computer as a control device, has an input resistance of about 1 M$\Omega$, and its input capacitance is no more than 30 pF.

The measurement data recovered with the voltage measurement device 1 are displayed and stored in the evaluation unit 15. The data can be shown in two-dimensional form on a display unit 21, either in real time or by reading out from the memory of the evaluation unit 15, and may be reproduced for comparison purposes or for assessment of the results of the treatment.

The representation can take place here as an instantaneous voltage signal, as a bar chart, or in optional other ways which are ergonomically favorable for the doctor performing the treatment.

Furthermore, the control unit 16 allocated to the evaluation unit 15 can effect the switching off or the reduction of the power delivered by the HF generator 11 when the measured voltage signal falls below a predetermined threshold value $U_{g1}$ 17, in order to thus prevent the catheter or the surroundings heating up without thereby producing the desired ablation. The threshold value $U_{g1}$ 17 can be changed, and thus very accurately predetermined, in dependence on the respective instantaneous delivered ablation power or integrated delivered ablation power, i.e., delivered ablation energy. By this means, a contamination of the catheter with coagulated substances can be reduced to a considerable degree or prevented.

Furthermore, the control device 16 can begin, when a further threshold value $U_{g2}$ 18 is exceeded at the beginning of the ablation process, to integrate the power delivered by the HF generator 11 until the voltage signal falls either below the threshold value $U_{g1}$ 17 or below an optional other predeterminable value. By this means, the value associated with the energy delivery into the tissue is determined which enables the doctor performing the treatment to make statements concerning the ablation effect. It furthermore falls within the scope of the invention to carry out the integration of the power 11 delivered by the HF generator, multiplied by the height of the voltage signal, in order to arrive at an improved or corrected statement concerning the ablation effect.

It likewise falls within the scope of the invention to take into account further functional values in dependence on the instantaneous voltage $U_1$ in the integration of the power delivered by the HF generator, such as for example the tabulated functional values of the lesion effects for a standardized catheter 3 or for an individual catheter 3, as determined by standard measurements, for example.

If a parameter obtained for a given catheter type, or for an individual catheter, is available for the determination of the lesion effect, the depth of the lesion can also be displayed as a function of the delivered energy and used for shutting off the lesion process. Coordinated with the respective catheter electrode, the possibility is thereby afforded to the doctor performing the treatment of defining locally different depths, or given depths and lengths, of the lesions produced, to set them on the control device 16, and subsequently to convert them in an automated manner during the treatment.

Instead of the automated switching off, an optical or acoustic signal can be given to the doctor performing the treatment, which supports him during the performance of the treatment and which does not impede the further carrying out of the ablation, for example, based on EKG data.

If with a very high delivery of energy, evaporation or vaporization is effected within the tissue to be treated, as a rule a voltage peak is formed, which was measured as peak 20 in FIG. 1. Such processes can according to the invention be used by means of determining the time differential and/or the absolute value of the course of the potential, or by means of a function in dependence on both measured values, as control magnitudes in order to interrupt the supply of high frequency energy associated with the process, or at least locally to reduce it.

It furthermore falls within the scope of the invention to embody the control device 16 by means of an external computer or a personal computer 19.

The invention is likewise not limited to high frequency catheter ablation, but can be applied with success in most other catheter ablation processes for the monitoring of the result of the respective treatment.

LIST OF REFERENCE SYMBOLS

1 voltage measuring apparatus
2 low pass filter
3 catheter
4 neutral electrode
5 $U_0$ base signal
6 signal flank (rising)
7 tissue
8 signal shoulder
9 signal flank (falling)
10 $U_i$ increased base signal
11 HF generator
12 ablation control equipment
13 trough
14 blood, liquid
15 evaluation unit
16 control device
17 $U_g$ threshold value
18 $U_g$ threshold value
19 personal computer
20 peak
21 display unit

KEYS OF THE FIGURES

Figure 4:
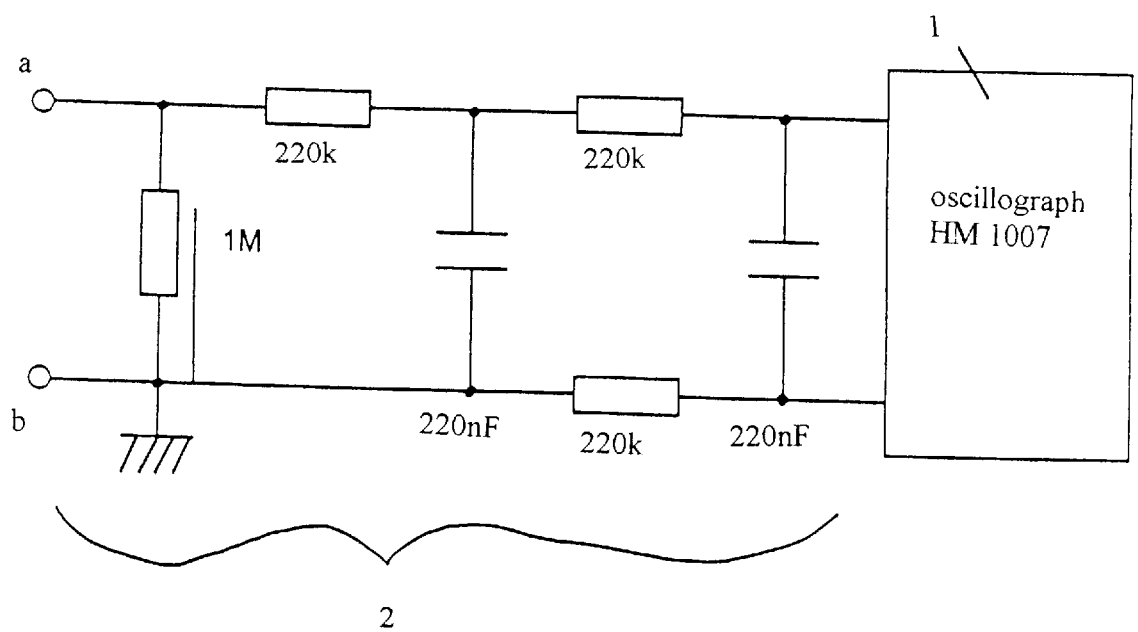
FIG. 4 shows a low pass filter, which can be used together with an oscilloscope for the recovery of the voltage signal according to the invention.

FIG. 2
11 HF generator (pulsed) connection box
3 catheter . . . electrodes a, b
2 low pass filter control/switching off
15 evaluation
19 pc with monitor for display, recording, data evaluation
  display unit
  optical display
  acoustic display
FIG. 3
11 HF generator
12 HF control 2000 connection box
3 catheter
4 neutral electrode
7 tissue
FIG. 4
1 oscillograph HM 1007
FIG. 6
  [Graph of] Integrated Potential vs. Depth
  [Abscissa]: Depth (mm)
  [Ordinate]: Integrated potential [mV * s]

What is claimed is:

1. Process for the determination of at least one of the interaction and the contact of a catheter arranged in a patient's vessel, particularly in a patient's blood stream, with the patient's tissue, characterized by the detection of the voltage signals which arise when an electrode of the catheter at least one of comes into contact, and stays in contact, with the patient's tissue.

2. Process according to claim 1, wherein the detection of the voltage signals includes their measurement with a high-ohmic measuring device, which preferably has an input resistance of at least 500 KΩ.

3. Process for HF catheter ablation, in which tissue sections of a patient to be treated are ablated by the irradiation of high frequency power, furthermore including a process according to claim 1 for the detection of at least one of the contact between the catheter and the patient's tissue and of the temperature of the patient's tissue.

4. Process according to claim 3, characterized in that the catheter used for ablation has available several, separately controllable, ablation electrodes, at which the voltage signals appear, or includes further separately connected electrodes which are respectively allocated to ablation electrodes, wherein the voltage signals are detected at the separate ablation electrodes or at the allocated electrodes.

5. Process according to claim 3, characterized in that the voltage signals are detected during the performance of the HF ablation, wherein the high frequency signals for ablation are applied either continuously or in a pulsed manner.

6. Process according to claim 3, characterized in that the voltage signals are detected during the delivery of the HF power, and when a threshold value is fallen below or exceeded, effect the switching off or at least the reduction of the delivery of the high frequency power.

7. Process according to claim 3, characterized in that the high frequency power delivered by the catheter is integrated over time, as long as the voltage signal is situated above a predetermined threshold, and the integrated power is calculated and displayed as ablation energy hitherto delivered into the tissue.

8. Process according to claim 7, characterized in that on reaching a predetermined ablation energy value, the delivery of high frequency power to the allocated catheter electrode is shut off or at least reduced.

9. Process according to claim 3, characterized in that the course of the voltage signals and also of the delivered and/or of the time integrated ablation power is displayed and stored, allocated to the respective catheter electrode.

10. Process according to claim 3, characterized in that the voltage signal which appears is displayed optically and/or acoustically, wherein the optical display takes place in the form of bar charts, real time representation of the voltage signals in a two-dimensional coordinate system and/or in a display of time-integrated power data.

11. Apparatus, in particular for the carrying out of processes according to claim 1, characterized by a device (1) for detection of a voltage on at least one catheter electrode (a, b), wherein the voltage between the catheter electrode (a, b) and a further electrode (a, b, 4) is measured, wherein the further electrode is a neutral electrode (4) which remains in contact with the body of the patient to be treated, or a further electrode (a, b) installed on the catheter (3).

12. Apparatus according to claim 11, characterized in that the voltage measurement takes place substantially with such a high-ohmic input that no currents appear which disturb the ablation or the measurement of the EKG signals.

13. Apparatus according to claim 11, characterized in that the catheter electrodes (a, b) attached to the voltage measuring device (1), and the neutral electrode (4), all consist of platinum or are coated with platinum.

14. Apparatus according to claim 11, characterized in that the voltage measuring device (1) has an input resistance of at least more than 100 KΩ and preferably several MΩ.

15. Apparatus according to claim 14, characterized in that the voltage measuring device (1) has an input resistance of about 1 megohm and an input capacitance of no more than 30 pF.

16. Apparatus according to claim 11, characterized in that the measurement of the voltage can be carried out by means of the voltage measuring device (1) during the delivery of the high frequency ablation power.

17. Apparatus according to claim 11, characterized in that the ablation catheter (3) includes high frequency ablation electrodes (a, b) consisting of platinum or coated with platinum, at which the voltage signals for recognizing the catheter-tissue contact and/or the tissue temperature are taken off.

18. Apparatus according to claim 11, further characterized by a low pass filter (2) for the suppression of interferences of the high frequency ablation signals and also of ripple interference.

19. Apparatus according to claim 11, further characterized by a device (15) for the display and storage of the voltage signals, and also preferably also of the delivered high frequency ablation power and energy.

20. Apparatus according to claim 19, characterized in that the course of the voltage signals and also the instantaneously delivered and/or the time-integrated ablation power are displayed and stored, allocated to the respective catheter electrodes (a, b).

21. Apparatus according to claim 19, further characterized by a device (16, 19) for the display and/or evaluation of the voltage signals, by means of which the voltage signals which arise are displayed optically or acoustically, wherein the optical display preferably takes place in the form of bar charts, real time representation of the voltage signal in a two-dimensional coordinate system, and/or by the display of power data which are integrated over time.

22. Apparatus according to claim 11, further characterized by a device (15, 16, 19) by means of which the voltage signals are detected during the delivery of the high frequency power and, in the case that the voltage signal falls below a preassignable, settable threshold value ($U_g$, 17), the switching off, or at least the reduction, of the delivery of the high frequency power is effected.

23. Apparatus according to claim 11, further characterized by a device (18, 19) by which the high frequency power delivered by the catheter is integrated over time, as long as the voltage signals are situated above a predetermined threshold value ($U_g$, 18) and by which the integrated power is calculated and displayed as ablation energy delivered into the tissue hitherto, or attained interaction with the tissue, or attained ablation depth in the tissue.

24. Apparatus according to claim 23, further characterized in that on reaching a predetermined value of ablation energy delivered into the tissue hitherto, or attained interaction with the tissue or attained depth of ablation, the delivery of high frequency power to the associated catheter electrode is switched off or at least reduced.

* * * * *